United States Patent [19]

Wands et al.

[11] Patent Number: 5,212,085

[45] Date of Patent: May 18, 1993

[54] SF-25 COLON ADENOCARCINOMA ANTIGEN, AND ANTIBODIES WITH RECOGNIZE THIS ANTIGEN

[75] Inventors: Jack R. Wands, Walrun, Mass.; Hiroshi Takahashi, Tokyo, Japan

[73] Assignee: The General Hospital Corporation, Boston, Mass.

[21] Appl. No.: 203,198

[22] Filed: Jun. 7, 1988

Related U.S. Application Data

[63] Continuation-in-part of Ser. No. 130,777, Dec. 9, 1987, abandoned.

[51] Int. Cl.[5] .................. C12N 5/20; C12N 15/02; C07K 15/28; C12P 21/08
[52] U.S. Cl. .................. 435/240.27; 530/388.85; 530/387.7; 530/389.7; 530/391.3; 435/70.21; 435/172.2
[58] Field of Search .............. 530/387, 388.85, 388.8, 530/389.7, 391.3, 387.7; 435/240.27, 172.2, 70.21

[56] References Cited

U.S. PATENT DOCUMENTS

| | | |
|---|---|---|
| 4,444,744 | 4/1984 | Goldenberg . |
| 4,485,093 | 11/1984 | Runge ........................ 424/85.91 |
| 4,536,479 | 8/1985 | Vander-Mallie . |
| 4,571,382 | 2/1986 | Adachi . |
| 4,661,586 | 4/1987 | Levy et al. . |
| 4,683,200 | 7/1987 | Hirohashi et al. . |
| 4,695,538 | 9/1987 | Cote et al. . |
| 4,877,611 | 10/1989 | Cantrell ........................... 424/88 |

OTHER PUBLICATIONS

Muaro et al. Caner Res. 48:4888-4596 1988.
Goding "Monoclonal Antibodies:Principles and Practice" Academic Press, 1983 pp. 118-125.
Takahashi, H. et al., *Cancer Res.* 48:6573-6579 (1988).
Wilson, B. E. et al., *Hepatology* 7(5): Abstract No. 416 (1987).
Wilson, B. et al., *Proc. Natl. Acad. Sci. USA.* 85: 3140-3144 (1988).
Neville et al., *Hum. Pathol.* 13:1067-1081 (1982).
Levy et al., *Ann. Rev. Med.* 34:107-110 (1983).
Herlyn et al., *Proc. Natl. Acad. Sci. USA* 76:1438-1442 (1979).
D. M. Herlyn et al., *Canc. Res.* 40:717 (1980).
Chang et al., *Hybridoma* 1:37 (1981).
Steplewski et al., *Canc. Res.* 41:2723 (1982).
D. M. Herlyn et al., *Int. J. Canc.* 27:769 (1981).
D. Herlyn et al., *Proc. Natl. Acad. Sci. USA* 79:4761 (1982).
Atkinson et al., *Canc. Res.* 42:4820 (1982).
Maganai et al., *Science* 212:55 (1981).
Maganai et al., *J. Biol. Chem.* 257:14365 (1982).
Magnani, J. L., et al., *Canc. Res.* 43:5489-5492 (1983).
Sears et al., *Lancet ii* 762 (1982).
Finan et al., *Br. J. Cancer* 46:9 (1982).
Thompson et al., *Br. J. Cancer* 47:595 (1983).
Lindholm et al., *Intl. Arch. Allergy Appl. Immunol.* 71: 178 (1983).
Stramignoni et al., *Int. J. Cancer* 31:543 (1983).
Shen et al., *Int. J. Cancer* 33:465 (1984).
Kaszubowski et al., *Canc. Res.* 44:1194 (1984).
Koprowski et al., *Proc. Natl. Acad. Sci. USA* 81:216 (1984).
Herlyn, M., et al., *J. Immunol. Meth.* 80:107-116 (1985).
Sakamoto et al., *Fed. Proc.* 44:792 (1985).
Shi et al., *Canc. Res.* 44:1142 (1984).
Fukushima et al., *Canc. Res.* 44:55279 (1984).
Lan et al., *Canc. Res.* 45:305 (1985).
Drewinko et al., *Canc. Res.* 46:5137 (1986).

(List continued on next page.)

*Primary Examiner*—David L. Lacey
*Assistant Examiner*—Paula Hutzell
*Attorney, Agent, or Firm*—Sterne, Kessler, Goldstein & Fox

[57] ABSTRACT

The present invention pertains to the SF-25 antigen of colon adenocarcinoma cells, to functional derivatives of this antigen, and to antibodies and antibody fragments capable of binding this antigen. The invention further discloses methods of diagnosing and treating colon cancer which employ the above molecules.

12 Claims, 3 Drawing Sheets

OTHER PUBLICATIONS

Hand et al., *Canc. Res.* 45:833 (1985).
Johnson et al., *Canc. Res.* 46:850 (1986).
Paterson et al., *Int. J. Cancer* 37:659 (1986).
Muraro et al., *Int. J. Cancer* 39:34 (1987).
Bleday et al., *Cancer* 57:433 (1986).
Wands et al., *Gastroenterol.* 80:225 (1981).
Carlin et al., *Exp. Cell. Res.* 147:359 (1983).
Moriarty et al., *Hybridoma* 2:39 (1983).
He et al., *In Vitro* 20:493 (1984).
Carlson et al., *J. Clin. Invest.* 76:40 (1985).
Shouval et al., *Hepatology* 5:347 (1985).
Hu et al., *Hepatology* 6:1396 (1986).
Wiedmann et al., *Hepatology* 7:543 (1987).
Anderson et al., *Science,* 220:542 (1983).
Macklis et al., *Brain Res.* 359:158 (1985).
Mew et al., *Canc. Res.* 45:4380 (1985).
Oseroff et al., *Proc. Natl. Acad. Sci. USA* 83:8744 (1986).
Oseroff et al., *Photochem. Photobiol.* 46:83 (1987).
Esteban et al., *J. Nucl. Med.* 28:861 (1987).
Hobbs et al., *J. Dermatol. Surg. Oncol.* 13:955 (1986).
Manyak et al., *J. Clin. Oncol.* 6:380 (1988).

SF-25 COLON ADENOCARCINOMA ANTIGEN, AND ANTIBODIES WITH RECOGNIZE THIS ANTIGEN

CROSS REFERENCE TO RELATED APPLICATIONS

This application is a continuation of U.S. patent application Ser. No. 130,777, now abandoned which was filed on Dec. 9, 1987.

BACKGROUND OF THE INVENTION

1. Field of the Invention

The present invention is directed toward the SF-25 antigen of colon adenocarcinoma cells, and to antibodies, and in particular, monoclonal antibodies, which are reactive against this antigen. The invention is further directed toward continuous hybridoma cell lines capable of secreting such monoclonal antibodies, and to methods of using these antibodies.

2. Background of the Invention

The ability to generate monoclonal antibodies has enabled the identification of tumor-associated antigens. Monoclonal antibodies of relevant specificities can be valuable reagents not only for immunodiagnosis and immunotherapy, but also in the study of tumor cells in general. Examples of various neoplasms to which monoclonal antibodies have been generated include leukemia (Seon et al., *Proc. Natl. Acad. Sci., USA* 80:845 (1983); Aota et al., *Cancer Res.* 43:1093 (1983); Royston et al., *TransDlan. Proc.* 13:761 (1981)); glioma (Bourdin et al., *Canc. Res.* 43:2796 (1983); Schnegg et al., *Canc. Res.* 41:1209 (1981)); melanoma (Dippold et al., *Proc. Natl. Acad. Sci., USA* 77:6114 (1980); Carrel et al., *Canc. Res.* 40:2523 (1980)); breast carcinoma (Colcher et al., *Proc. Natl. Acad. Sci., USA* 78:3199 (1981); Schlom et al., *Proc. Natl. Acad. Sci., USA* 77:6841 (1980)); lung carcinoma (Cuttitta et al., *Proc. Natl. Acad. Sci., USA* 78:4591 (1981)); cervical carcinoma (Handley et al., PCT Publication No. WO 83/04313 (1983)); bladder carcinoma (Masuko et al., *J. Natl. Cancer Instit.* 72:523 (1984); Messing et al., *J. Urol.* 132:167 (1984); Grossman, *J. Urol.* 130:610 (1983); Stramignoni et al., *Intl. J. Cancer* 31:543 (1983); Herlyn et al., *Proc. Natl. Acad. Sci., USA* 76:1438 (1979); Kasai et al., *J. Surg. Res.* 30:403-408 (1981)); and prostate carcinoma (Ware et al., *Canc. Res.* 42:1215 (1982); Starling et al., *Canc. Res.* 42:3714 (1982)). The detection and characterization of human tumor antigens using monoclonal antibodies has been reviewed by Lloyd, "Human Tumor Antigens: Detection and Characterization with Monoclonal Antibodies," In: Herberman, ed., *Basic and Clinical Tumor Immunology* I:159-214, Nijoff, Boston (1983). Lloyd's review includes a discussion of the use of monoclonal antibodies to detect colorectal cancer. Lloyd, supra, at 181-182.

Colon and rectal cancers accounts for approximately 20% of all deaths due to malignant disease in the United States. The cause of colorectal carcinoma, which affects men and women approximately equally, is not known. Despite advances in management of colorectal cancer, the death rate for this disease is the same today as it was 40 years ago. The most significant factor in the poor prognosis for colorectal carcinoma is delay in diagnosing the disease. Because symptoms of colorectal carcinoma are frequently vague and nonspecific in the early stages of the disease, detection is often delayed. As a result, the cancer is often so well established by the time a positive diagnosis is made that a cure is difficult or impossible. Thus, for example, patients whose tumor is confined to the bowel wall generally have an excellent chance for cure following surgical resection (five-year survival rate>95%). Where the tumor has extended to the serosa and mesenteric fat, however, the five-year survival rate following resection declines to 80%. Lymph node metastases reduce the five-year survival rate to 40%, while distant metastases (e.g., liver, lung, bone, brain) reduce the five-year survival rate to zero.

Commonly used screening tests for colorectal carcinoma contribute to delayed detection of the disease. For example, the guaiac test, which detects occult blood in the stool, requires that a colonic malignancy be advanced to the bleeding stage before it can be detected. Moreover, this test suffers from low and variable sensitivity due to dye instability. Sigmoidoscopy requires that any colorectal carcinoma be visible, and diagnosis may be complicated by the presence of other lesions such as hemorrhoids, polyps, and proctitis. Colonoscopy has similar drawbacks.

The inadequacies of presently available screening methods may be one reason that many colorectal cancers are first diagnosed as a result of a complication of the original lesion. For example, a bowel wall may be perforated by the tumor, causing acute peritonitis. Obviously, in such a case, the cancer will be well advanced by the time a diagnosis is made.

Delayed detection, then, is a major factor contributing to an overall five-year survival rate of only approximately 50% for colorectal malignancies. The diagnosis and treatment of colorectal cancer is described in LaMont et al., "Disease of the Small and Large Intestine," In: Petersdorf et al., eds., *Harrison's Principles of Internal Medicine* 10th Edition, McGraw Hill, Publisher, New York, pp. 1762-1765 (1983).

Colorectal carcinomas generally respond poorly to chemotherapy. Although palliation may be effected, chemotherapy has not been shown to prolong the lives of patients diagnosed as having colorectal cancer, especially when the disease is widely disseminated. DeVita, "Principles of Cancer Therapy," In: *Harrison's Principles of Internal Medicine.* supra at 783 and Table 125-7.

The potential specificity of monoclonal antibodies for antigenic determinants associated with human tumor cells has led researchers and clinicians to investigate monoclonal antibodies for diagnostic and therapeutic use in the management of colorectal cancer. The potential clinical usefulness of monoclonal antibodies includes the detection of human cancers by immunohistochemistry (Gatter et al., *Semin. Oncol.* IX:517-525 (1982); Herlyn et al., *Proc. Natl. Acad. Sci., USA* 76:1438-1442 (1979)), radioimaging (Neville et al., *Hum. Pathol.* 13:1076-1081 (1982)), and the use of monoclonal antibodies as therapeutic agents (Levy et al., *Ann Rev. Med.* 34:107-110 (1983)).

For example, Sakamoto et al. (European Patent Publication No. 0 119 556 A2), disclose the use of a panel of monoclonal antibodies raised in mice immunized with human gastrointestinal tumors to diagnose the presence of colon cancer. These monoclonal antibodies recognize antigenic determinants present on normal as well as cancerous gastrointestinal cells. Although it is stated that these monoclonal antibodies can be used to treat gastrointestinal tumors, the significant cross-reactivity of these monoclonal antibodies with normal tissue minimizes their therapeutic utility. The antigens recognized by this panel of monoclonal antibodies were either glycoproteins or glycolipids having molecular weights of 25 Kd, 29 Kd, 52 Kd, or 95 Kd. Four of the 12 monoclonal antibodies were of class IgM. The IgM monoclonal antibody showing the best reactivity with colon carcinoma cells (12/17) cross-reacted with pancreatic cancer, breast cancer, bovarian cancer, and lung cancer cells. Moreover, it cross-reacted with normal adult tissue from lung, liver, gallbladder, esophagus, colon, pancreas, ureter, breast, prostate, sweat glands, and secretions.

Lindholm et al., Intl. Arch. Allergy Appl. Immunol. 71:178 (1983), immunized mice with a colorectal adenocarcinoma cell line for liver metastasis membranes from a patient having colon adenocarcinoma to produce monoclonal antibodies. Three monoclonal antibodies of class IgM were identified that reacted with colorectal adenocarcinoma cell lines, extracts of pooled adenocarcinomas and individual gastrointestinal tumors, but not with other cell types. The antigen complex was identified as a monosialoganglioside, but the antigen was not characterized further.

Koprowski et al., U.S. Pat. No. 4,349,528, describe the production of a monoclonal antibody specific for commercial carcinoembryonic antigen (CEA) having a molecular weight of about 180 Kd. The monoclonal antibody did not bind to antigens of colorectal carcinoma cells having molecular weights other than 180 Kd. r Sakamoto et al., Fed. Proc. 44(3):792 (Abstract 2222) (1985), describe antigens from human colon carcinoma which reacted with monoclonal antibodies obtained by immunization with cultured human colon and pancreas carcinomas, or with lysates of colon cancer cells. Two of the antigens K-314 (gp170) and V-215 (gp140) were detected only on colon and a few lung cancer cell lines. Neither the class of monoclonal antibodies involved nor the individual specificities of these monoclonal antibodies with respect to the antigens is disclosed.

Herlyn et al., Proc. Natl. Acad. Sci., USA 76(3):1438 (1979), describe the detection of a colorectal carcinoma-specific antigen using monoclonal antibodies (1083-17 and 1116-56) detected 8/9 human colorectal carcinomas. No data are presented characterizing the physical or chemical characteristics of the antigen involved. Both monoclonal antibodies were of class IgM.

Magnani et al., Science 212:55 (1981), describe the partial characterization of an antigen present on colon carcinoma cells which reacts with a monoclonal antibody. The molecular weight of the antigen, which was not purified to homogeneity, was not determined, although it was concluded that the antigen was a monosialoganglioside based upon its chemical reactivity and susceptibility to certain enzymes. The antigen was also found in human meconium, a rich source of normal fetal glycolipids.

Steplewski et al., Canc. Res. 41:2723 (1981), describe the release of monoclonal antibody-defined antigens by human colorectal carcinoma and melanoma cells. Some of the antigens detected were released into the tissue culture, while others could not be detected in tissue culture supernatants. It is stated that a monosialoganglioside antigen was released by tumor cells, but not by normal colon tissue, and that this antigen was not found in the serum of normal individuals. However, the antigen is not characterized further. Three other monoclonal antibodies (NS-3a-22, NS-10, and NS-33a) reacted with a glycolipid antigen released by most colorectal carcinoma cells. Two of these (NS-33a and NS-10) were of isotype IgM.

Herlyn et al., Intl. J. Cancer 27:769 (1981), studied the complement-dependent cytotoxicity of four hybridoma cell lines (NS-10, NS-33a, NS-38a, and NS-38c), which produced colon carcinoma-specific antibodies of isotype IgM. These monoclonal antibodies showed complement-dependent cytotoxicity against colon carcinoma cells.

Chang et al., Hybridoma 1:37 (1981), describe the detection of a monoclonal antibody-defined colorectal carcinoma antigen using a solid-phase binding inhibition radioimmunoassay. Two of the monoclonal antibodies were reported to be specific for antigen present on colorectal carcinoma. This antigen could be extracted from colon carcinoma cells using 3M KCl and was a glycolipid.

The diagnostic use of monoclonal antibodies in colorectal carcinoma is reviewed by Lloyd, suora, and by Davis et al., In: Prasad et al., eds., Novel Approaches to Cancer Chemotherapy, Academic Press, New York (1984) (see, e.g., Table III at page 43, setting forth tumor-associated antigens of gastrointestinal and colorectal tumors (among others) identified by various investigators.

As the above discussion demonstrates, despite long-standing scientific interest in the development of monoclonal antibodies to human colorectal carcinoma antigens, a need has continued to exist for a monoclonal antibody that shows a high degree of specificity for colorectal carcinoma. Such a monoclonal antibody should show no significant cross-reactivity with either normal human tissues or other malignant cell types.

SUMMARY OF THE INVENTION

The present invention relates to monoclonal antibody SF-25 and to its uses in the diagnosis and treatment of colon adenocarcinoma.

In detail, the invention concerns a molecule capable of binding to the SF-25 antigen of a colon adenocarcinoma cell, the molecule being selected from the group consisting of:

(a) an antibody substantially free of natural contaminants;

(b) a monoclonal antibody;

(c) a fragment of (a) or (b).

The invention also includes a hybridoma cell line capable of secreting a monoclonal antibody, the antibody being capable of binding to the SF-25 antigen of a colon adenocarcinoma cell.

The invention also pertains to a hapten capable of binding to an antibody, said antibody being capable of binding the SF-25 antigen of a colon adenocarcinoma cell.

The invention also provides a method of detecting whether an animal contains a colon adenocarcinoma cell which comprises:

(a) contacting tissue of the animal that is suspected of containing said cell with a detectably labeled molecule capable of binding to an SF-25 antigen of a colon adenocarcinoma cell, and (b) detecting any of said molecule bound to the antigen.

The invention additionally includes a method of suppressing the growth of a colon adenocarcinoma cell in an animal which comprises administering to the animal a therapeutically effective amount of a molecule capable of binding the SF-25 antigen of a colon adenocarcinoma cell.

DESCRIPTION OF THE PREFERRED EMBODIMENT

The present invention derives from the discovery of a novel antigen designated "SF-25" that is expressed on the surface of human adenocarcinoma cells of the colon. The identification of this novel antigen, and the capacity to bind the antigen with antibodies or fragments of antibodies, provide a method for diagnosing the presence of adenocarcinomas of the colon. In addition, the SF-25 antigen and antibodies capable of binding the SF-25 antigen provide a method for suppressing the growth of adenocarcinoma cells of the colon.

I. General Characteristics of SF-25 Antigen

Figure 1:
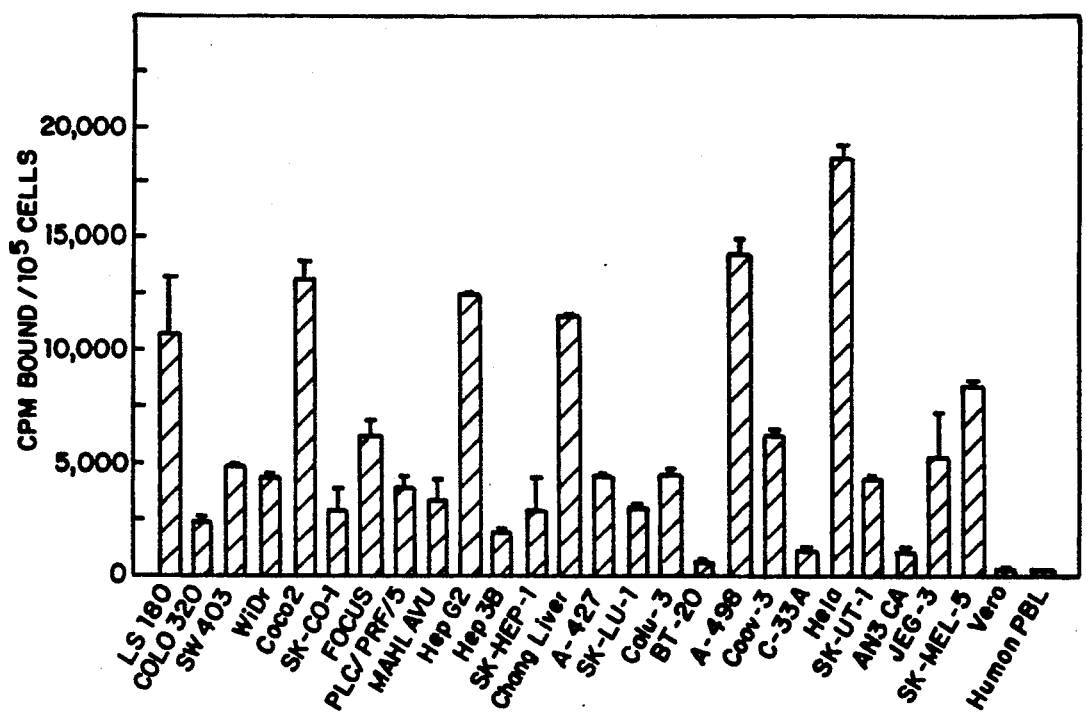
FIG. 1 shows a display of $^{125}$I-SF-25 binding to antigens expressed on various tumor cell lines (Table 1).

The antigen identified by MAb SF-25 appears to be novel and heretofore not previously described. Some of the more interesting features are: 1) Its constitutive expression on colon adenocarcinomas in vivo and relative uniform distribution in most if not all tumor cells. 2) The epitope to which SF-25 binds appears quite labile and sensitive to mild fixation, denaturing gels and detergent extraction. 3) The epitope resides on the cell surface and is a protein with a molecular weight of approximately 125 kd as shown by $^{125}$I-labeling experiments and subsequent immunoprecipitation with the SF-25 Mab followed by SDS polyacrylamide gel electrophoresis. This finding is in contrast to most previously described antigens associated with gastrointestinal malignancies where further characterization has revealed a mucin glycoprotein or glycolipid structure (Johnson, U. G., et al. *Canc. Res.* 56:850–857 (1986); Lun, M., et al., *Canc. Res.* 45:305–310 (1985); Pant, K. D., et al., *Immunol. Commun.* 6:411–421 (1977); Magnani, J. L., et al., *J. Biol. Chem.* 257:14365–14369 (1982); Shi, Z. A., et al., *Canc. Res.* 44:1142–1147 (1984); Fukushima, K., et al., *Canc. Res.* 44:5279–5285 (1984)). In this regard, some of the characteristics of SF-25 antigen may be due in part to the immunizing cell type. The FOCUS cell line was derived from a human hepatocellular carcinoma and it would not be expected to secrete large amount of mucin glycoproteins (Lun, H., et al., *In Vitro* 20:493–504 (1984)). 4) The antigen is most closely associated with the malignant phenotype and appears not to be expressed on an adjacent normal colon or other normal tissues with the exception of a subpopulation of distal tubular cells of the kidney. SF-25 binds to 6/6 colon and hepatoma cell lines as well as several others (FIG. 1). Thus, the epitope is not confined to a specific tumor cell type and reflects an antigen most closely associated with malignant transformation.

The SF-25 antigen is different from those previously described antigens associated with adenocarcinomas of the colon. For example, the well characterized carcinoembryonic antigen (CEA) is a glycoprotein of higher molecular weight (MW=180 kd) (Westwood, J. H., et al., *Immunochem.* 11:811–818 (1974)). CA19-9 recognizes a carbohydrate determinant found on both mucin glycoproteins and lipids (Magnani, J. L., et al,. *Science* 212:55–56 (1981); Magnani, J. L., et al., *Canc. Res.* 43:5489–5492 (1983)). CO29.11 detects a sialylated Lewis a (Le$^a$) antigen but is directed towards a different epitope and has a higher binding affinity than CA19-9 (Herlyn, M., et al., *J. Immunol. Met.* 80:107–116 (1985)). Similarly, DU-PAN-2 detects a mucin-like antigen isolated from a human pancreatic adenocarcinoma (lb). Monoclonal antibodies directed against such antigens do not uniformly react with all adenocarcinomas of the colon by immunoperoxidase staining (Atkinson, B. F., et al., *Canc. Res.* 42:4820–4823 (1982)) or by direct binding assays. The finding may be due in part to the fact that many of the MAbs bind to epitopes representing post-translational modification of "normal cellular" proteins and not to primary gene products associated with malignant transformation. These large "tumor associated" antigens are generally stable following formaldehyde fixation and paraffin embedding. In addition, CEA, CA 19-9, DU-PAN-2, and CO 29.11 represent cell products that are secreted or shed into cell culture supernatants from the immunizing cell type. They are often in the serum of patients with a variety of gastrointestinal malignancies (Herlyn, M., et al., *J. Immunol. Met.* 80:107–116 (1985); Atkinson, B. F., et al., *Canc. Res.* 42:4820–4823 (1982); Del Villano, B. C., et al., *Clin. Chem.* 29:549–552 (1983); Metzger, R. A., et al., *Proc. Natl. Acad. Sci. USA* 81:5242–5246 (1984)). In contrast, SF-25 antigen was not identified in cell culture supernatants from hepatoma and colon adenocarcinoma cell lines or in the serum of patients with gastrointestinal malignancies by a "simultaneous sandwich" homologous immunoradiometric assay (Wands, J. R., et al., *Proc. Natl. Acad. Sci. USA* 78:1214–1218 (1981)).

Another well characterized monoclonal antibody, designated B72.3 was produced against a membrane rich fraction of a metastasis derived from a mammary carcinoma (Colcher, D. P., et al., *Proc. Natl. Acad. Sci. USA* 78:3199–3203 (1981)). This antibody detects a large mucin glycoprotein TAG-72 (tumor associated glycoprotein) of >1000 kd molecular weight (Johnson, U. G., et al., *Canc. Res.* 56:850–587 (1986)). The antigen was expressed in only 1 of 18 colon cancer cell lines (Horan Hand, P., et al., *Canc. Res.* 45:833–840 (1985)) but it was detected, in vivo, in 80–85% of colon adenocarcinomas and their metastasis (Stramignoni, D., et al., *Int. J. Canc.* 31:543–552 (1983)). The in vivo distribution was found to be quite heterogenous as shown by immunoperoxidase staining of formaldehyde fixed paraffin embedded tissue specimens. Binding of B72.3 to its epitope on TAG-72 was substantially reduced by neuraminidase digestion and this suggests that sialic acid is an important structural component of the epitope (Johnson, U. G., et al., *Canc. Res.* 56:850-587 (1986)). TAG-72 antigen was also found in the serum of patients with gastrointestinal malignancies (Paterson, A. J., et al., *Int. J. Canc.* 37:659-666 (1986)). Another antibody produced against a 200 kd antigen residing on a membrane fraction derived from a primary colon adenocarcinoma cell line has also been described (Muraro, R., et al., *Int. J. Canc.* 39:34-44 (1987)). However, antigen expression appears to correlate with a more differentiated state and therefore, is highly expressed on normal colon and less on the transformed phenotype.

There is, however, one previously described MAb with some similar features to SF-25. The 17.1A antibody was produced against a colorectal adenocarcinoma cell line (Herlyn, M., et al., *Proc. Natl. Acad. Sci. USA* 76:1438-1442 (1979)) and detects a labile antigen sensitive to methanol, ethanol and formaldehyde fixation and paraffin embedding (Shen, J., et al., *Int. J. Canc.* 33:465-468 (1984)). Furthermore, the antigen is resistant to neuraminidase treatment and binding activity is abolished by protease treatment which suggests a non-mucin, non-sialic acid structure with respect to the 17.1A binding domain. Furthermore, the antigen is displayed on the distal convoluted tubular cells of the kidney like SF-25 and is expressed on most adenocarcinomas of the colon in situ by immunoperoxidase staining of fresh frozen tissue sections; the molecular weight, however, is about 40,000 daltons. MAb 17.1A appears different from SF-25 antigen since it is highly expressed on normal colon and small bowel as well as pancreas, gall bladder, cystic duct and sweat glands (Shen, J., et al., *Int. J. Canc.* 33:463-468 (1984)). The 17.1A IgG2a antibody is of particular interest since it apparently has potential for in vivo immunotherapy of colon adenocarcinoma (Herlyn, D. M., et al., *Canc. Res.* 40:717-721 (1980); Herlyn, D. M., et al., *Proc. Natl. Acad. Sci. USA* 79:4761-4765 (1982); Sears, H. F., et al., *Lancet* 1:762-765 (1982); Koprowski, H., et al., *Proc. Natl. Acad. Sci. USA* 81:216-219 (1984)). Recently a chimeric mouse-human construct has been produced by recombinant DNA techniques and the hybrid demonstrates the same biologic and antigen binding properties as the native molecule (Shaw, D. R., et al., *J. Immunol.* 138:4534-4538 (1987)).

Finally, there are a number of other monoclonal antibodies described that react with adenocarcinomas of the colon both in vitro and in vivo (Bleday, R., et al., *Cancer* 57:433-440 (1986); Finan, P. J., et al., *Br. J. Canc.* 46:9-17 (1982); Thomson, C. H., et al., *Br. J. Canc.* 47:595-605 (1983); Lindholm, L., et al., *Int. Arch. Allergy Appl. Immunol.* 71:178-181 (1983); Koszubowski, P. A., et al., *Canc. Res.* 44:1194-1199 (1984); Drewinko, B., et al., *Canc. Res.* 46:5137-5143 (1986)). Some of them are directed against glycoprotein determinants (Bleday, R., et al., *Cancer* 57:433-440 (1986); Koszubowski, P. A., et al., *Canc. Res.* 44:1194-1199 (1984)) and limited specificity testing to date suggest that they are quite different from the SF-25 antigen described herein. Such antibodies have been produced in an attempt to distinguish between the antigenic properties of the normal colon epithelial cell and its transformed phenotype. In this regard a mucin glycoprotein antigen designated "Large External Antigen" (LEA) has recently been described (Bleday, R., et al., *Cancer* 57:433-440 (1986)); it appears to be constitutively expressed on 17/17 colon cancer by immunoperoxidase staining of fresh tissue but was not found on adjacent normal colon. This antigenic determinant identified by Mab ND-1 was neuraminidase sensitive and is expressed on fetal colon and biliary epithelium as well as normal cervix and uterus. The authors speculate that LEA is a mucine glycoprotein associated with the malignant phenotype.

Figure 2:
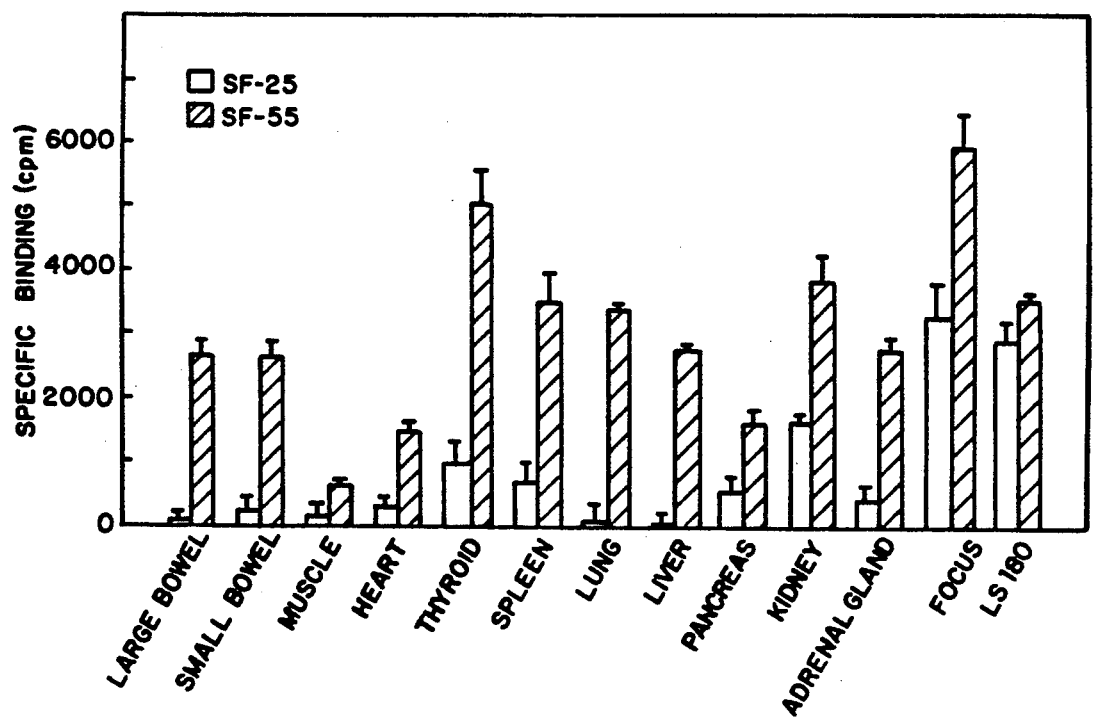
FIG. 2 shows the comparative binding of $^{125}$I-SF-25 to membranes prepared from normal tissues, a colon adenocarcinoma (LS-180), and focus cells (immunizing cell type). $^{125}$I-SF-55 is another monoclonal antibody produced against focus cells but which recognizes an antigen present on all human tissue and tumor cell lines.
Figure 3:
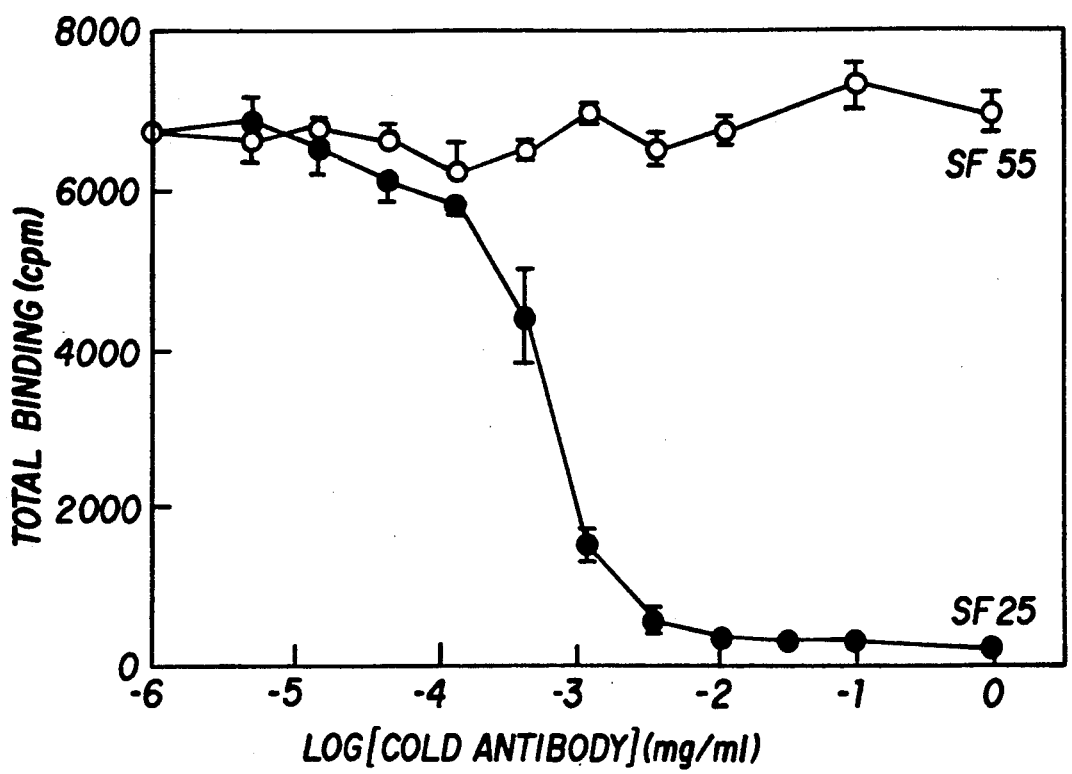
FIG. 3 shows a demonstration of $^{125}$I-SF-25 binding specificity to LS-180 cells by non-radioactive SF-25 antibody.

The SF-25 antigen is likely to be a primary gene product since it is constitutively expressed in all (17/17) adenocarcinoma of the colon studied thus far and not on adjacent normal colon. The antigen is displayed on the cell surface as shown by direct binding studies with live cells (FIGS. 2 and 3). $^{125}I$ cell labeling experiments provides further evidence for its location on the surface of malignant cells. Thus, the epitope would be accessible for binding with $^{125}I$-labeled SF-25 in vivo. More importantly, there appears to be little heterogeneity of antigen distribution among tumor cells within the colon tumor or between different tumors. The antigen is not shed into culture medium from colon adenocarcinoma cell lines or present in serum of patients bearing colorectal cancers at least in amounts detectable by a radioimmunometric assay. Thus, radiolabeled antibody may reach the tumor cell surface without being trapped in immune complexes. It is possible that SF-25 binds to a conformationally related or discontinuous epitope on the 125 kd protein. This epitope appears not to be a product of post-translational modifications which may explain in part its constitutive and homogenous localization to the coloni malignant phenotype.

II. The SF-25 Antigen

The novel antigen, SF-25, can be purified to be substantially free of natural contaminants through the use of any of a variety of methodologies. As used herein, a compound (such as an antibody, an antigen, a hapten, or fragments of such molecules) is said to be "substantially free of natural contaminants" if it has been substantially purified from materials with which it is normally and naturally found. The SF-25 antigen may be purified through application of standard chromatographic separation technology. Alternatively, and more preferably, the SF-25 antigen may be purified using immunoaffinity chromatography (Rotman, A., et al., *Biochim. Biophys. Acta* 641:114-121 (1981); Sairam, M. R., *J. Chromatog.* 215:143-152 (1981); Nielsen, L. S., et al., *Biochemistry* 21:6410-6415 (1982); Vockley, J., et al., *Biochem. J.* 217:535-542 (1984); Paucha, E., et al., *J. Virol.* 51:670-681 (1984); Chong, P., et al., *J. Virol. Meth.* 10:261-268 (1985)).

As will be readily appreciated by those of skill in the art, the purified SF-25 protein may be fragmented to produce "functional derivatives" useful in accordance with the methods of the present invention. Additionally, purified SF-25 (or fragments thereof) may be analyzed to determine their amino acid sequence. The availability of such sequence information permits the production of SF-25 antigen (or its fragments) by synthetic chemical techniques.

As used herein, a "functional derivative" of SF-25 antigen is a compound which possesses a biological activity (either functional or structural) that is substantially similar to a biological activity of SF-25. A molecule is said to be "substantially similar" to another molecule if both molecules have substantially similar structures or if both molecules possess a similar biological activity. The "functional derivatives" of SF-25 include both "fragments" and "variants" of SF-25. The term "fragment of SF-25" is meant to refer to any polypeptide subset of that molecule. The term "variant of SF-25" is meant to refer to a molecule substantially similar in structure to either the entire molecule, or to a fragment thereof provided that the "variant" has at least one biological activity that is either similar to an activity of SF-25 or inhibitory to an activity of SF-25. Thus, provided that a molecule possesses at least one biological activity that is either similar to an activity of SF-25 or inhibitory to such an activity, it is considered a "variant" of the SF-25, as that term is used herein, even if one of the molecules contains one or more amino acids not found in the other, or if the sequences of amino acid residues in the two molecules are not identical.

III. SF-25 Antibodies and Antibody Fragments

In the following description, reference will be made to various methodologies well-known to those skilled in the art of immunology. Standard reference works setting forth the general principles of immunology include the work of Klein, J. (*Immunology: The Science of Cell-Noncell Discrimination,* John Wiley & Sons, New York (1982)); Kennett, R., et al. (*Monoclonal Antibodies, Hybridoma: A New Dimension in Biological Analyses,* Plenum Press, New York (1980)); Campbell, A. ("Monoclonal Antibody Technology," In: *Laboratory Techniques in Biochemistry and Molecular Biology,* Volume 13 (Burdon, R., et al., eds.), Elsevier, Amsterdam (1984)); and Eisen, H. N., (In: *Microbiology,* 3rd Ed. (Davis, B. D., et al., Harper & Row, Philadelphia (1980)).

An antibody is said to be "capable of binding" a molecule if it is capable of specifically reacting with the molecule to thereby bind the molecule to the antibody. As used herein, the term "hapten" is intended to refer to any molecule capable of being bound by an antibody. The term "epitope" is meant to refer to that portion of a hapten which can be recognized and bound by an antibody. A hapten or antigen may have one, or more than one epitope. An "antigen" is a hapten which is additionally capable of inducing an animal to produce antibody capable of binding to an epitope of that antigen. The specific reaction referred to above is meant to indicate that the hapten will react, in a highly selective manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding a hapten. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

The antibodies of the present invention may be prepared by any of a variety of methods. For example, cells expressing the SF-25 antigen can be administered to an animal in order to induce the production of sera containing polyclonal antibodies that are capable of binding the SF-25 antigen. In a preferred method, a preparation of SF-25 antigen is prepared and purified to render it substantially free of natural contaminants. Such a preparation is then introduced into an animal in order to produce polyclonal antisera of greater specific activity.

In the most preferred method, the antibodies of the present invention are monoclonal antibodies (or hapten binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N.Y., pp. 563-681 (1981)). In general, such procedures involve immunizing an animal (preferably a mouse) with SF-25 antigen or, more preferably, with an SF-25-expressing cell. Although any such cell may be employed in accordance with the present invention, it is preferable to employ the hepatocellular carcinoma cell line, FOCUS (Lun, H., et al., *In Vitro* 20:493-504 (1984)). Suitable cells can be recognized by their capacity to bind anti-SF-25 antibody. Such cells may be cultured in any suitable tissue culture medium; however, it is preferable to culture cells in Earle's modified Eagle's medium supplemented with 10% fetal bovine serum (inactivated at 56° C.), and supplemented with 10 μg/l of nonessential amino acids, 1,000 U/ml of penicillin, and 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands, J. R., et al. (*Gastroenterology* 80:225-232 (1981), which reference is herein incorporated by reference). The hybridoma cells obtained through such a selection are then assayed to identify clones which secrete antibodies capable of binding the SF-25 antigen. A preferred hybridoma cell line, obtained by this process, is the monoclonal antibody-producing cell line "SF-25." This cell line produces monoclonal antibody "SF-25" which is capable of binding to the SF-25 antigen. Cell line "SF-25" was deposited under the provisions of the Budapest Treaty with the American Type Culture Collection, 12301 Parklawn Drive, Rockville, Md., on Dec. 8, 1987, and given the ATCC designation: HB 9599.

Through application of the above-described methods, additional cell lines capable of producing antibodies which recognize epitopes of the SF-25 antigen can be obtained.

Alternatively, additional antibodies capable of binding to the SF-25 antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, antibodies capable of binding the SF-25 antigen are used to immunize an animal. The splenocytes of such an animal are then used to produce hybridoma cells, and the hybridoma cells are screened to identify clones which produce antibody whose ability to bind to anti-SF-25 antibody can be specifically blocked by the SF-25 antigen. Such antibodies comprise anti-idiotypic antibodies to the anti-SF-25 antibody. Such antibodies can be used to immunize an animal, and thereby induce the formation of anti-SF-25 antibodies. Since anti-idiotypic antibodies can be used to immunize an animal and thus provoke the production of anti-SF-25 antibodies, they provide one method for inducing, or enhancing, an animal's immune response to colon cancer.

It will be appreciated that Fab and F(ab')$_2$ and other fragments of the antibody of the present invention may be used according to the methods disclosed herein for the detection and treatment of colon adenocarcinoma in the same manner as intact antibody. Such fragments are typically produced by proteolytic cleavage, using enzymes such as papain (to produce Fab fragments) or pepsin (to produce F(ab')$_2$ fragments). Alternatively, hapten-binding fragments can be produced through the application of recombinant DNA technology or through synthetic chemistry.

IV. Production of the SF-25 Antigen by Recombinant Technology

The identification of the amino acid sequence of the SF-25 antigen (or its functional derivatives) permits these molecules to be produced through the application of recombinant DNA techniques. For example, an oligonucleotide can be constructed which is capable of encoding the SF-25 antigen (or its functional derivatives). Such an oligonucleotide can be operably linked into an expression vector and introduced into a host cell to enable the expression of the SF-25 antigen (or functional derivatives of this antigen) by that cell. Techniques for synthesizing such oligonucleotides are disclosed by, for example, Wu, R., et al., *Proc. Nucl. Acid. Res. Molec. Biol.* 21:101-141 (1978)). Procedures for constructing recombinant molecules in accordance with the above-described method are disclosed by Maniatis, T., et al., In: *Molecular Cloning: A Laboratory Manual,* Cold Spring Harbor Press, Cold Spring Harbor, N.Y. (1984), which reference is herein incorporated by reference.

The identification of the amino acid sequence of the SF-25 antigen, or fragments of this antigen, also permits the cloning of the gene which encodes the SF-25 antigen.

Any of a variety of methods may be used to clone the SF-25 gene. One such method entails analyzing a shuttle vector library of cDNA inserts (derived from an SF-25 expressing cell) for the presence of an insert which contains the SF-25 gene. Such an analysis may be conducted by transfecting cells with the vector, and then assaying for SF-25 expression. A preferred method for cloning the SF-25 gene entails determining the amino acid sequence of the SF-25 molecule. Although it is possible to determine the entire amino acid sequence of the SF-25 molecule it is preferable to determine the sequence of peptide fragments of the molecule. If the peptides are greater than 10 amino acids long, this sequence information is generally sufficient to permit one to clone a gene such as the gene for the SF-25 molecule. To accomplish this task, SF-25 molecules are preferably purified from producer cells by monoclonal antibody affinity chromatography and isolated by preparative sodium dodecyl sulfate-polyacrylamide gel electrophoresis ("SDS-PAGE") and electroelution. The SF-25 molecules are fragmented as with cyanogen bromide, or with proteases such as papain, chymotrypsin, trypsin, etc. (Oike, Y., et al., *J. Biol. Chem.* 257:9751-9758 (1982); Liu, C., et al., *Int. J. Pept. Protein Res.* 21:209-215 (1983)). The resulting peptides are separated, preferably by reverse-phase HPLC, and subjected to amino acid sequencing. To accomplish this task, the protein is preferably analyzed by automated sequenators.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene,* 3rd Ed., W. A. Benjamin, Inc., Menlo Park, Calif. (1977), pp. 356-357). Using the genetic code, one or more different oligonucleotides can be identified, each of which would be capable of encoding the SF-25 peptides. The probability that a particular oligonucleotide will, in fact, constitute the actual SF-25-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1-12 (1985). Using the "codon usage rules" of Lathe, a single oligonucleotide, or a set of oligonucleotides, that contains a theoretical "most probable" nucleotide sequence capable of encoding the SF-25 peptide sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the SF-25 fragment is used to identify the sequence of a complementary oligonucleotide or set of oligonucleotides which is capable of hybridizing to the "most probable" sequence, or set of sequences. An oligonucleotide containing such a complementary, sequence can be employed as a probe to identify and isolate the SF-25 gene (Maniatis, T., et al., *Molecular Cloning A Laboratory Manual,* Cold Spring Harbor Press, Cold Spring Harbor, N.Y. (1982).

A suitable oligonucleotide, or set of oligonucleotides, which is capable of encoding a fragment of the SF-25 gene (or which is complementary to such an oligonucleotide, or set of oligonucleotides) is identified lusing the above-described procedure), synthesized, and hybridized by means well known in the art, against a DNA or, more preferably, a cDNA preparation derived from cells which are capable of expressing the SF-25 gene. Single stranded oligonucleotide molecules complementary to the "most probable" SF-25 peptide encoding sequences can be synthesized using procedures which are well known to those of ordinary skill in the art (Belagaje, R., et al., *J. Biol. Chem.* 254:5765-5780 (1979); Maniatis, T., et al., In: *Molecular Mechanisms in the Control of Gene Expression,* Nierlich, D. P., et al., Eds., Acad. Press, NY (1976); Wu, R., et al., *Proc. Nucl. Acid Res. Molec. Biol.* 21:101-141 (1978); Khorana, R. G., *Science* 203:614-625 (1979)). Additionally, DNA synthesis may be achieved through the use of automated synthesizers. Techniques of nucleic acid hybridization are disclosed by Maniatis, T., et al. (In: *Molecular Cloning, A Laboratory Manual.* Cold Spring Harbor Laboratories, Cold Spring Harbor, N.Y. (1982)), and by Haymes, B. D., et al. (In: *Nucleic Acid Hybridization, A Practical Approach,* IRL Press, Washington, DC (1985)), which references are herein incorporated by reference. The source of DNA or cDNA used will preferably have been enriched for SF-25 sequences. Such enrichment can most easily be obtained from cDNA obtained by extracting RNA from cells, such as hepatoma cells, which produce high levels of SF-25. An example of such a cell is a FOCUS cell (Lun, H., et al., *In Vitro* 20:493–504 (1984)).

To identify and clone the gene which encodes the SF-25 protein, a DNA, or more preferably a cDNA, library is screened for its ability to hybridize with the oligonucleotide probes described above. Suitable DNA preparations (such as human genomic DNA) are enzymatically cleaved, or randomly sheared, and ligated into recombinant vectors. The ability of these recombinant vectors to hybridize to the above-described oligonucleotide probes is then measured. Vectors found capable of such hybridization are then analyzed to determine the extent and nature of the SF-25 sequences which they contain. Based purely on statistical considerations, a gene such as that which encodes the SF-25 molecule could be unambiguously identified (via hybridization screening) using an oligonucleotide probe having only 18 nucleotides.

Thus, in summary, the actual identification of SF-25 peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate the SF-25 gene.

Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In a alternative way of cloning the SF-25 gene, a library of expression vectors is prepared by cloning DNA or, more preferably, cDNA (from a cell capable of expressing SF-25) into an expression vector. The library is then screened for members capable of expressing a protein which binds to anti-SF-25 antibody, and which has a nucleotide sequence that is capable of encoding polypeptides that have the same amino acid sequence as SF-25, or fragments thereof. In this embodiment, DNA, or more preferably cDNA, is extracted and purified from a cell which is capable of expressing SF-25 antigen. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing SF-25 in order to produce a prokaryotic genomic expression vector library. Procedures for preparing cDNA and for producing a genomic library are disclosed by Maniatis, T., et al. (*Molecular Cloning: A Laboratory Manual*, Cold Spring Harbor Press, Cold Spring Harbor, N.Y. (1982)).

The above-described expression vector genomic library is used to create a bank of host cells (each of which contains one member of the library). The expression vector may be introduced into the host cell by any of a variety of means (i.e., transformation, transfection, protoplast fusion, electroporation, etc.). The bank of expression vector-containing cells is clonally propagated, and its members are individually assayed (using an immunoassay) to determine whether they produce a protein capable of binding to anti-SF-25 antibody.

The expression vectors of those cells which produce a protein capable of binding to anti-SF-25 antibody are then further analyzed to determine whether they express (and thus contain) the entire SF-25 gene, whether they express (and contain) only a fragment of the SF-25 gene, or whether they express (and contain) a gene whose product, though immunologically related to SF-25, is not SF-25. Although such an analysis may be performed by any convenient means, it is preferable to determine the nucleotide sequence of the DNA or cDNA fragment which had been cloned into the expression vector. Such nucleotide sequences are then examined to determine whether they are capable of encoding polypeptides having the same amino acid sequence as digestion fragments of SF-25.

An expression vector which contains a DNA or cDNA molecule which encodes the SF-25 gene may, thus, be recognized by: (i) the ability to direct the expression of a protein which is capable of binding to anti-SF-25 antibody; and (ii) the presence of a nucleotide sequence which is capable of encoding each of the fragments of SF-25. The cloned DNA molecule of such an expression vector may be removed from the expression vector and isolated in pure form.

IV. Expression of the Cloned SF-25 Gene

The present invention therefore provides a means for obtaining a DNA molecule which encodes the SF-25 molecule. By operably linking this DNA molecule (or a fragment or mutated form of this DNA molecule) to a functional promoter, it is possible to direct the expression of the SF-25 gene (or a functional derivative thereof) in a cell, or organism.

The expression of a DNA sequence requires that the DNA sequence be "operably linked" to DNA sequences which contain transcriptional and translational regulatory information. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Regulatory regions in eukaryotic cells will in general include a promoter region sufficient to direct the initiation of RNA synthesis.

Two DNA sequences (such as a promoter region sequence and a SF-25-encoding sequence) are said to be operably linked if the nature of the linkage between the two DNA sequences does not (1) result in the introduction of a frame-shift mutation, (2) interfere with the ability of the promoter region sequence to direct the transcription of the SF-25-encoding sequence, or (3) interfere with the ability of the SF-25-encoding sequence to be transcribed by the promoter region sequence. Thus, a promoter region would be operably linked to a DNA sequence if the promoter were capable of transcribing that DNA sequence.

To express the SF-25 molecule (or a functional derivative thereof) in a prokaryotic cell (such as, for example, E. coli, B. subtilis, Pseudomonas, Streptomyces, etc.), it is necessary to operably link the SF-25-encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)), the promoters of the bacteriophages of *Bacillus* (Gryczan, T. J., In: *The Molecular Biology of the Bacilli,* Academic Press, Inc., NY (1982)), and *Streptomyces* promoters (Ward, J. M., et al., *Mol. Gen. Genet.* 203:468–478 (1986)). Prokaryotic promoters are reviewed by Glick, B. R., (*J. Ind. Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell requires the presence of a ribosome binding site upstream of the gene-encoding sequence. Such ribosome binding sites are disclosed, for example, by Gold, L., et al. (*Ann. Rev. Microbiol.* 35:365–404 (1981)).

If expression is desired in a eukaryotic cell, such as yeast, fungi, mammalian cells, or plant cells, then it shall be necessary to employ a promoter capable of directing transcription in such a eukaryotic host. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)).

As is widely known, translation of eukaryotic mRNA is initiated at the codon which encodes the first methionine of an oligonucleotide. For this reason, it is preferable to ensure that the linkage between a eukaryotic promoter and an oligonucleotide which encodes the SF-25 molecule (or a functional derivative thereof) does not contain any intervening codons which are capable of encoding a methionine (i.e., AUG). The presence of such codons results either in a formation of a fusion protein (if the AUG codon is in the same reading frame as the SF-25 encoding oligonucleotide) or a frame-shift mutation (if the AUG codon is not in the same reading frame as the SF-25 gene sequence).

An oligonucleotide which encodes the SF-25 protein (or a functional derivative thereof) when operably linked to a functional promoter is preferably introduced into a recipient cell by any of a variety of suitable means: transformation, transfection, conjugation, protoplast fusion, electroporation, etc.

The SF-25-encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the SF-25 polypeptide may occur through the transient expression of the introduced gene sequence. Alternatively, permanent expression may occur through the integration of the introduced gene sequence into the host chromosome.

Preferably, the introduced gene sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Maniatis, T., et al. (In: *Molecular Cloning, A Laboratory Manual,* Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli,* Academic Press, NY (1982), pp. 307–329). Suitable *Streptomyces* plasmids include pIJ101 (Kendall, K. J., et al., *J. Bacteriol,* 169:4177–4183 (1987)), and streptomyces bacteriophages such as φC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol,* 33:729–742 (1978)).

Preferred eukaryotic plasmids include BPV, vaccinia, SV40, 2-micron circle, etc. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance,* Cold Spring Harbor Laboratory, Cold Spring Harbor, N.Y., p. 445-470 (1981); Broach, J. R., *Cell* 28:203-204 (1982); Bollon, D. P., et al., *J. Clin. Hematol. Oncol.* 10:39-48 (1980); Maniatis, T., In: *Cell Biology: A Comprehensive Treatise, Vol.* 3, *Gene Expression*, Academic Press, NY, pp. 563-608 (1980)).

VI. Diagnostic Uses of SF-25 Antibodies and Antibody Fragments

The antibodies (or fragments thereof) of the present invention are particularly suited for use in immunoassays wherein they may be utilized in liquid phase or bound to a solid-phase carrier.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope. Its use may have substantial advantages since its avoids the problem of dehalogenation of the $^{125}$I or $^{131}$I-labeled monoclonal antibody by the liver. In addition, this radionucleotide has a more favorable gamma emission energy for imaging (Perkins, A. C., et al., *Eur. J. Nucl. Med.* 10:296-301 (1985); Carasquillo, J. A., et al., *J. Nucl. Med.* 28:281-287 (1987)). For example, $^{111}$In coupled to monoclonal antibodies with 1-(P-isothiocyanatobenzyl)-DPTA have shown little uptake in non-tumorous tissues, particularly the liver and therefore enhance specificity of tumor localization (Esteban, J. M., et al., *J. Nucl. Med.* 28:861-870 (1987)).

Examples of suitable non-radioactive isotopic labels include $^{157}$Gd, $^{55}$Mn, $^{162}$ $^{52}$Tr, $^{56}$Fe, etc.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1-31 (1976)), and Schurs, A. H. W. M., et al. (*Clin. Chim. Acta* 81:1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to SF-25. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The antibodies, or fragments of antibodies, of the present invention may be used to quantitatively or qualitatively detect the presence of cells which express the SF-25 antigen. Such detection may be accomplished using any of a variety of immunoassays. For example, by radioactively labeling the antibodies or antibody fragments, it is possible to detect SF-25 antigen through the use of radioimmune assays. A good description of a radioimmune assay (RIA) may be found in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein.

The binding molecules of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, etc.) and a quantity of detectably labeled soluble antibody is added to permit detection and/or quantitation of the ternary complex formed between solid-phase antibody, antigen, and labeled antibody.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199-206 of *Radioim-*

*mune Assay Method*, edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplex labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

As explained above, the immunometric assays for antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

VII. Diagnostic Uses of SF-25 Antigen and Its Functional Derivatives

The present invention also provides a method for detecting the presence of antibodies which are specific to the SF-25 antigen. The presence of such antibodies in the sera of an animal would be indicative of that animal's prior or present exposure to cells expressing the SF-25 antigen. Thus, this method provides an alternative diagnostic test for colon cancer. Such a diagnostic test could be performed using either purified SF-25 antigen, a functional derivative of SF-25 antigen or an antibody which was anti-idiotypic to anti-SF-25 antibody. Fragments of such an idiotypic antibody could also be employed. Such molecules are preferably labeled (using any of the enzyme, radioisotopic, non-radioactive isotopic, fluorescent or chemiluminescent labels described above. Such an immunoassay may be performed by adapting the method of Fridlender, B. R. (U.S. Pat. No. 4,313,927). Thus, purified antigen or hapten (or anti-idiotypic antibody or fragments of such an antibody) is coupled or bound to a solid surface. Any of a variety of known coupling techniques may be modified to accomplish this goal. The immobilized surface to which these molecules are bound may be chosen from a wide variety of possible surfaces such as nylon, latex, glass, silica, polyethylene, polystyrene, polyvinylchloride or polycarbonate. The support material may have virtually any possible structural configuration so long as the coupled molecule is capable of binding to any anti-SF-25 antibody which is provided. Thus, the support configuration may be spherical, as in a bead, or cylindrical, as in the inside surface of a test tube, or the external surface of a rod. Alternatively, the surface may be flat such as a sheet, test strip, etc.

In one embodiment, a biological sample (such as, for example, blood, lymph, etc.) is assayed in the manner described above, to determine whether anti-SF-25 antibodies are present. In an alternative embodiment, a biological sample (such as a biopsy of colon tissue) is introduced into a test animal (such as, for example, a mouse) and the sera of the mouse analyzed to determine whether antibodies recognizing the SF-25 antigen have been elicited. Alternatively, the biological sample could be provided to splenocyte cells grown in tissue culture, and the resulting antibodies analyzed for their ability to bind SF-25 antigen. Any of the many known immunoassay techniques may be modified in accordance with these embodiments.

As used herein, an effective amount of a diagnostic reagent (such as an antibody, antibody fragment, or hapten) is one capable of achieving the desired diagnostic discrimination. The amount of such materials which are typically used in a diagnostic test are generally between 0.01–1 $\mu$g, and preferably between 0.1–1 $\mu$g.

VIII. Therapeutic Uses of the Present Invention

In addition to providing a method for diagnosing colon cancer, the present invention also provides a means for preventing the onset of colon cancer, and for treating infected animals. The discovery that the SF-25 antigen is expressed on colon cancer cells, and the identification of antibodies capable of binding to this antigen provides means for preventing and treating colon cancer. In one embodiment, the SF-25 antigen, an immunologically active fragment of this antigen, or an anti-idiotypic antibody, or fragment thereof is provided to an animal to thereby elicit the production of antibodies capable of recognizing SF-25-expressing cells.

The ability to label antibodies, or fragments of antibodies, with toxin labels provides an additional method for treating colon cancer. In this embodiment, antibodies, or fragments of antibodies which are capable of recognizing the SF-25 antigen are labeled with toxin molecules and administered to a patient suspected of having colon cancer. When such a toxin derivatized molecule binds to a colon cancer cell, the toxin moiety will cause the death of the cancer cell.

Any of a variety of toxin molecules may be employed to produce such labeled antibodies or labeled antibody fragments. Examples of suitable toxin labels include diphtheria toxin, ricin, and cholera toxin, etc. One preferred type of toxin molecule is a "photoactivatable toxin molecule." Examples of such "photo-activatable toxin molecules" include Photofrin II (Williams, R. D., et al., *Photochem. Photobiol.* 46:733-738 (1987); Mattielli, J., et al., *Photochem. Photobiol.* 46:873-880 (1987)), hematoporphyrin derivatives (Benson, R. C., *Urology* 31:13-17 (1988)), hemoglobin, and its derivatives (Polla, L. L., et al., *Ann. Dermatol. Venereol.* 114:497-505 (1987)); procion blue (Macklis, J. D., et al., *Brain Res.* 359:158-165 (1985)), fluorescent, and other dyes ( Miller, J. P., et al., *Science* 206: 702-704 (1979); Manyak, M. J., et al., *J. Clin. Oncol.* 6:380-391 (1988)), etc. The critical attribute of such molecules is that they be capable of greater absorption of light (at some wavelength) than the surrounding tissue.

In this therapy, termed "photothermolysis," photoactivation of the toxin is achieved by a careful selection of wavelength, pulse, and intensity of the light. The light energy absorbed by such molecules is released either as heat or emitted as light at a different wavelength. If a suitable light (such as, preferably, a laser light) is employed, the death of cells and tissue which contain the photoactivatable toxin will occur, either because of the amount of the heat released by this process, or because of the photo-oxidation of essential biological molecules in the cells or tissue by the emitted light. The physics of laser therapy and photothermolysis are reviewed by Hobbs, E. R., et al, (*J. Dermatolog Surg Oncol.* 13:955-964 (1987)), Anderson, R. R., et al. (*Science* 220:524-527 (1983)), Macklis, J. D., et al. (*Brain Res.* 359:158-165 (1985)), Wilson, B. C. (*Phys. Med. Biol.* 31:327-360 (1986)) and especially by Manyak, M. J., et al. (*J. Clin. Oncol.* 6:380-391 (1988)), all of which references are herein incorporated by reference.

By conjugating the antibodies of the present invention with a photo-activatable toxin, it is possible to direct the toxin molecule only to those cells which express a corresponding tumor-associated antigen. This method has been used to provide a selective means for treating a tumor without damage to normal (i.e. non-antigen expressing) cells. Examples of the use of this method are provided by Mew, D., et al. (*Cancer Res.* 45:4380-4386 (1985); *J. Immunol.* 130:1473-1477 (1983)); by Wat, C. -K., et al. (In: *Prog. Clin. Biol. Res.* Vol 170, (Doiron, D. R., et al., eds.), Alan R. Liss, NY, pp. 351-360 (1984)); and by Oseroff, A. R., et al. (*Photochem. Photobiol.* 46:83-96 (1987); *Photochem. Photobiol.* 43 Suppl.:105s (1986); *Photochem. Photobiol.* 41 Suppl.:75s (1985); *Photochem. Photobiol.* 41 Suppl.:35s (1985); *Proc. Natl. Acad. Sci. (USA)* 83:8744-8748 (1986); *Clin Res.* 33:674a (1985); *J. Invest. Dermatolog.* 84:335 (1985); all of which references are herein incorporated by reference).

The above-described photothermolysis therapy can be accomplished using any light source which is capable of photo-activating the toxin. The photo-activation of such toxins can thus be achieved using light sources other than lasers. For example, such photo-activation can be achieved using light from an ordinary light bulb (Dougherty, T. J., et al., *J. Natl. Canc. Inst.* 55:115-129 (1979); Wilson, B. C., *Phys. Med. Biol.* 31:327-360 (1986)). Photo-activation of the toxin may alternatively be achieved by the administration of a chemiluminescent agent (i.e. a light-emitting molecule) to an individual who has received the photo-activatable toxin. This embodiment of the present invention is particularly advantageous in the in situ treatment of gastric carcinomas, intestinal polyps, Barrett's esophagus. The embodiment may also be used for metastatic cancers (Phillip, M. J., et al., In: Porphyrin Localization and Treatment of Tumors (Doiron, D. R., et al., eds.), Alan R. Liss, NY, pp. 563-569 (1985)).

As would be understood by one of ordinary skill in the art, such compositions may contain salts, buffers, adjuvants, or other substances which are desirable for improving the efficacy of the composition. Adjuvants are substances that can be used to specifically augment a specific immune response. Normally, the adjuvant and the composition are mixed prior to presentation to the immune system, or presented separately, but into the same site of the animal being immunized. Adjuvants can be loosely divided into several groups based upon their composition. These groups include oil adjuvants (for example, Freund's complete and incomplete), mineral salts (for example, $AlK(SO_4)_2$, $AlNa(SO_4)_2$, $AlNH_4(SO_4)$, silica, kaolin, and carbon), polynucleotides (for example, poly IC and poly AU acids), and certain natural substances (for example, wax D from *Mycobacterium tuberculosis*, as well as substances found in *Corynebacterium parvum*, or *Bordetella pertussis*, and members of the genus *Brucella*. Among those substances particularly useful as adjuvants are the saponins such as, for example, Quil A. (Superfos A/S, Denmark). Examples of materials suitable for use in vaccine compositions are provided in *Reminqton's Pharmaceutical Sciences* (Osol, A., Ed., Mack Publishing Co., Easton, Pa., pp. 1324-1341 (1980)).

The therapeutic compositions of the present invention can be administered parenterally by injection, rapid infusion, nasopharyngeal absorption (intranasopharangeally), dermoabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

Many different techniques exist for the timing of the immunizations when a multiple administration regimen is utilized. It is possible to use the compositions of the invention more than once to increase the levels and diversities of expression of the immunoglobulin repertoire expressed by the immunized animal. Typically, if multiple immunizations are given, they will be given one to two months apart.

According to the present invention, an "effective amount" of a therapeutic composition is one which is sufficient to achieve a desired biological effect. Generally, the dosage needed to provide an effective amount of the composition will vary depending upon such factors as the animal's age, condition, sex, and extent of disease, if any, and other variables which can be adjusted by one of ordinary skill in the art.

The antigenic preparations of the invention can be administered by either single or multiple dosages of an effective amount. Effective amounts of the compositions of the invention can vary from 0.01–1,000 μg/ml per dose, more preferably 0.1–500 μg/ml per dose, and most preferably 10–300 μg/ml per dose.

Having now generally described the invention, the same will be more readily understood through reference to the following examples which are provided by way of illustration, and are not intended to be limiting of the present invention, unless specified.

EXAMPLE 1

Production of Monoclonal Antibody Producing Hybridoma Cells

The hepatocellular carcinoma cell line FOCUS was used to immunize mice. The cells were grown in Earle's modified Eagle's medium (M. A. Bioproducts, Walkerville, Md.) supplemented with 10% fetal bovine serum (inactivated at 56° C.), 10 μg/ml of non-essential amino acids, 1,000 U/ml of penicillin, and 100 μg/ml of streptomycin. An early passage of FOCUS cells from the original tumor had been kept in liquid nitrogen. This culture was subsequently regrown and harvested from monolayer culture. Cells were harvested from the monolayer cultures by washing three times with 20 mM phosphate-buffered saline (PBS), pH 7.2, followed by treatment with versene buffer in the absence of trypsin. The single cell suspensions, thus obtained, were used for immunization of Balb/c mice. Primary immunizations were accomplished intraperitoneally with $4.0 \times 10^6$ intact whole cells/ml in 50% complete Freund's adjuvant. After 6–10 weeks, secondary immunizations were performed by an intravenous inoculation of $4.0 \times 10^6$ cells in 200 μl of PBS. 3 days after the secondary immunization, the mice were sacrificed and splenocytes were recognized. The splenocytes were fused with the parent myeloma cell line (SP2O), selectively maintained in HAT medium, and then cloned by limiting dilution as described by Wands, J. R., et al. (*Gastroenterology* 80:225–232 (1981)).

The hybridomas which were obtained through the above-described procedure were screened for antibody activity on a panel of cell lines listed in Table 1. Subsequent specificity testing of cloned hybridomas was performed against various cell lines by both indirect and direct binding radioimmunoassays (RIAs).

The indirect radioimmunoassay was carried out in 96 well filterbottomed plates (U&P Scientific Inc., San Diego, Calif.). These plates were first filled with 100 μl of bovine serum for 30 minutes at room temperature in order to block non-specific protein binding sites. Next, $1 \times 10^5$ target cells (suspended in 100 μl of Earle's modified Eagle's medium and containing 20% fetal bovine serum) were incubated with 100 μl of fresh culture supernatant from 70% confluent hybridoma for 1 hour at room temperature with gentle agitation. Cells were drawn onto filters in the wells by suction, then washed three times with 0.2 ml of PBS containing 20% fetal bovine serum. Subsequently, $1 \times 10^5$ cpm of $^{125}$I-labeled sheep anti-mouse IgG/F(ab')$_2$ (New England Nuclear, Boston, Mass.) diluted in 100 μl PBS with 20% fetal bovine serum was added and allowed to incubate for 1 hour at room temperature with agitation. The cells were again washed three times with PBS/20% fetal bovine serum and the filters were dried and counted using a gamma well counter.

The direct RIA was performed using $^{125}$I-labeled monoclonal antibodies. Monoclonal antibodies were labeled with $^{125}$I or $^{131}$I using the Iodogen method (Fraker, P. J., et al., *Biochem. Biophys. Res. Commun.* 80:849–857 (1978)) to a specific activity of between 5–15 μCi/μg. Briefly, 50 μl aliquots of Iodogen (1,3,4,6-tetrachloro3α,6α-diphenylglycoluril; Pierce Chemical Co., Rockford, Ill.) at 50 μg/ml in chloroform were evaporated to dryness under nitrogen gas in $10 \times 75$ mm glass tubes. Na$^{125}$I or Na$^{131}$I (Amersham Corp., Searle Div., Arlington Heights, Ill.) and 100 μg of monoclonal antibody were added to the tubes, which were then incubated for 6 minutes at room temperature. The radiolabeled monoclonal antibody was then separated from free iodine on a PD-10 column (Pharmacia Fine Chemicals, Piscataway, N.J.) which had been previously equilibrated with 0.9% NaCl. Iodenated monoclonal antibodies were always tested to assure that there was no loss of their specificity or immunoreactivity by direct binding to FOCUS and other cell lines. Labeled monoclonal antibodies ($1 \times 10^5$ cpm) were incubated with $1 \times 10^5$ cells in 100 μl of PBS/20% fetal bovine serum for 1 hour at room temperature. The cells were then washed three times as described above and the radioactivity of the dried filters was determined. $^{125}$I-labeled, non-relevant monoclonal antibody (designated B$_2$TT (an anti-tetanus toxoid IgG$_1$ and IgG$_{2b}$)) was employed as a negative control. Only if the amount of radioactivity bound to anti-SF-25 antibody was greater than 2.5 times that bound by the control antibody were the results considered to indicate positive binding values.

In total, the above procedure resulted in the isolation of 90 clones capable of secreting antibodies against antigens present on FOCUS cells using the above described indirect binding assay. Among the 90 clones, 18 were shown to react with human colon carcinoma cell lines. One of the 18 antibody secreting clones was designated "SF-25" and was chosen for further investigation. The antibody produced by this hybridoma line was of an IgG$_{2b}$ isotype.

SF-25 monoclonal antibody (from double-cloned cell lines) were purified for further study by using a Sepharose 4B Staphylococcal protein A-affinity column (Pharmacia Fine Chemicals, Piscataway, N.J.). One to two ml of ascites fluid was placed on the column (which had been previously equilibrated with 0.1M sodium phosphate buffer (pH 8.0)). The ascites fluid was allowed to remain on the column for 60 minutes at 4° C. and then unbound material was washed extensively with the same phosphate buffer. Bound mouse IgG isotypes were eluted with 0.05M citrate buffer by a pH step gradient, using several void volumes, each of various pH (pH 6.0, pH 5.5, and pH 3.5), according to the method of Ey, P. L., et al. (*Immunochem.* 15:429–436 (1978)). Purified antibodies thus obtained were dialyzed overnight at 4° C. against twice-normal concentrated saline (0.3M NaCl) and the protein concentration was determined by the method of Lowry, O. H., et al. (*J. Biol. Chem.* 193:265–275 (1951)).

TABLE 1

| Origin of Cell Lines | |
|---|---|
| Cell Line | Tissue of Origin |
| LS 180 | Human, Colon, Adenocarcinoma |
| COLO 320 | Human, Colon, Adenocarcinoma |
| SW 403 | Human, Colon, Adenocarcinoma |
| WiDr | Human, Colon, Adenocarcinoma |
| CaCo-2 | Human, Colon, Adenocarcinoma |
| SK-Co-I | Human, Ascites, Colon Adenocarcinoma |
| FOCUS | Human, Liver, Hepatoma |
| PLC/PRF/5 | Human, Liver, Hepatoma |
| MAHLAVU | Human, Liver, Hepatoma |
| Hep G2 | Human, Liver, Hepatoma |

TABLE 1-continued

Origin of Cell Lines

| Cell Line | Tissue of Origin |
| --- | --- |
| Hep 3B | Human, Liver, Hepatoma |
| SK-HEP-1 | Human, Ascites, Hepatoma |
| Chang Liver | Human, Liver, Epithelial-like morphology |
| A-427 | Human, Lung, Adenocarcinoma |
| SK-LU-1 | Human, Lung, Adenocarcinoma |
| Calu-3 | Human, Pleural effusion, Lung adenocarcinoma |
| BT-20 | Human, Breast, Adenocarcinoma |
| A-498 | Human, Kidney, Carcinoma |
| Caov-3 | Human, Ovary, Adenocarcinoma |
| C-33A | Human, Cervix, Undifferentiated carcinoma |
| HeLa | Human, Cervix, Adenocarcinoma |
| SK-UT-1 | Human, Uterine, Mesodermal tumor |
| AN3 CA | Human, Endometrium, Adenocarcinoma |
| JEG-3 | Human, Choriocarcinoma |
| SK-MEL-5 | Human, Lymph node, Malignant melanoma |
| Vero | Monkey, Kidney, Fibroblast-like morphology |

EXAMPLE 2

SF-25 Cell Binding Studies

The binding specificity of monoclonal antibody SF-25 was investigated by direct radioimmunoassay (described in Example 1) using a panel of cell lines. As shown in FIG. 1, SF-25 monoclonal antibodies reacted with all the hepatoma cell lines tested (FOCUS, PCL/PRF/5, MAHLAVU, SK-HEP-1, HepG2 and HEP3B) as well as Chang liver cells. More importantly, 6 of 6 colon adenocarcinoma cell lines expressed the SF-25 antigen on their cell surfaces. Additional specificity testing revealed that SF-25 did not bind to normal human lymphocytes nor to vivo cells (African green monkey kidney cells). Weak binding was observed with cell lines BT-20, C-33A and AN3CA. Higher binding was observed with SK-MEL-5 and A-498 (see FIG. 1).

EXAMPLE 3

Membrane Binding Studies

Membrane fractions were prepared from normal human tissues as well as from colon adenocarcinomas and adjacent normal colon obtained from surgical specimens. Human colon adenocarcinoma cell line (LS180) or hepatoma cell line (FOCUS) grown as solid tumors in nude mice served as a positive control. Such xenografts were performed as follows: 4-6 week old male Balb/c nu/nu mice were injected subcutaneously in the left shoulder with $1 \times 10^8$ LS-180 cells or FOCUS cells in 0.2 ml of PBS to establish solid tumors. These solid tumors were passed from animal to animal by transplanting with a 2-mm$^3$ piece of an explanted LS-180 tumor obtained from an existing tumor bearing mouse. Tumors were subjected to membrane preparations and SF-25 biodistribution nuclear imaging studies when they grew to a size of approximately $10 \times 10$ mm. Tissues were homogenized with a Polytron homogenizer in ten volumes of 20 mM PBS, pH 7.2 containing 0.1% NaN3 and were centrifuged at 20,000 g for 30 minutes. Homogenization and centrifugation were repeated three times. Subsequently, the pellets were resuspended in PBS containing 20% glycerol and frozen at $-80°$ C. until further use. For the binding assay, membrane preparations were diluted to a protein concentration of 1 mg/ml with 20% calf serum PBS. Direct binding assays were performed in 96-well filter plates as described above using 100 μl of membrane preparation. Binding specificity was always confirmed by competitive inhibition with the same "cold" antibody and not by a non-relevant Mab directed against a different cell surface antigenic determinant (SF-55).

The capability of $^{125}$I-SF-25 monoclonal antibody to bind to membrane preparations from FOCUS and LS-180 tumors as well as other normal human tissue is shown in FIG. 2.

Figure 4:
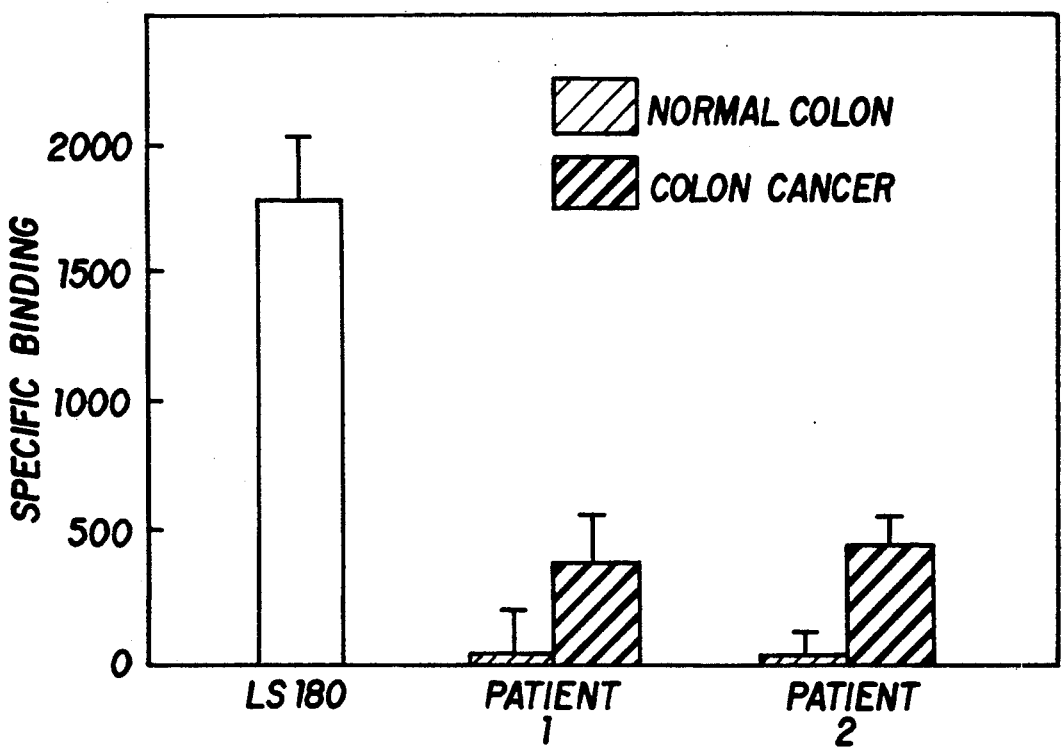
FIG. 4 shows the direct binding of $^{125}$I-SF-25 to membrane preparations derived from adenocarcinomas of the colon and the adjacent normal colon. Specific normal binding refers to CPM-bound, that is, inhibited by cold SF-25 but not SF-55 (monoclonal antibody control). The protein concentration of all membrane preparations placed on the filter was the same.

Specific binding (defined as cpm bound in the presence and absence of "cold" SF-25 antibody) was observed to both FOCUS and LS-180 membranes but not to membranes derived from other normal human tissues with the notable exception of kidney. Binding was inhibited by "cold" SF-25 but not by "cold" SF-55. SF-55 is an antibody reactive against a highly expressed common cell surface membrane antigen. The results of this experiment are shown in FIG. 3. This experiment demonstrated that $^{125}$I-SF-55 was able to bind to FOCUS and LS-180 as well as other normal tissues and thus could serve as a good positive control for comparison with SF-25 (FIG. 2). Using these two monoclonal antibodies, membrane binding studies on surgical specimens of human colon adenocarcinomas were performed, and the results compared to the adjacent normal counterpart. The results of this comparison are shown in FIG. 4. Specific binding of SF-25 to membrane preparation were observed in LS-180 tumors and human colon adenocarcinomas. In contrast, SF-25 showed no binding to membrane preparations of the normal colon mucosal counterpart. These results demonstrate that SF-25 binds specifically to antigens present on tumors in vivo and that these antigens were not detectable on membranes derived from the adjacent normal colon.

EXAMPLE 4

Immunoperoxidase Staining Studies

Tissue expression of the antigenic determinants recognized by SF-25 in vivo was further investigated by the avidin-biotin complex immunoperoxidase staining reaction. Staining of tissue sections from 17 colon adenocarcinoma along with normal mucosal counterparts were tested.

Tumors, adjacent normal counterparts and normal tissues were obtained fresh from surgery or as rapidly as possible from autopsies, and were immediately frozen in liquid nitrogen and stored at $-80°$ C. In some experiments, sections were cut from these snap-frozen tissues embedded in OCT compound (Miles Scientific, Naperville, Ill.), dried onto glass slides, fixed in cold acetone for 5 minutes and equilibrated with 10 mM PBS, pH 7.5. In other experiments, tissues were fixed in 2% paraformaldehyde for 2 hours and embedded in OCT compound or paraffin. When paraffin-embedded tissues were used, slides were deparaffinized with xylene and rehydrated by passage through graded alcohols to final wash in 10 mM PBS, pH 7.5. The tissue section was stained with the Vectastain ABC Kit (Vector Laboratories Inc., Burlingame, Calif.) as follows: Diluted normal horse serum (2% in 10 mM PBS, pH 7.5) was added to the slide and incubated at room temperature for 20 minutes to eliminate the non-specific binding of antibodies. The horse serum was removed by blotting and MAb containing ascites fluid diluted at 1:500 with 1% normal horse serum-/10 mM PBS, pH 7.5 was added to the slides. After an overnight incubation at 4° C., the slides were washed in 10 mM PBS, pH 7.5 for 20 minutes. Biotinylated anti-mouse IgG (0.01 mg/ml in 10 mM pBS, pH 7.5 containing 1% normal horse serum) was added to each slide and incubated for 60 minutes at room temperature. After washing with PBS for 20 minutes the tissue sections were incubated in 0.3% $H_2O_2$ in methanol for 20 minutes to block endogenous peroxidase and subsequently washed for 30 minutes in PBS. The slides were incubated with 0.5 mg/ml 3,3'-diaminobenzidine in 0.05M tris-phosphate buffer, pH 7.5 with 0.01% hydrogen peroxide until the positive controls showed evidence of a reaction. After washing with distilled water the tissues were counterstained with methyl-green or hematoxyline. Anti-HBs $IgG_{2b}$ ($B_2TT$) was used as a negative control MAb (Wands, J. R., et al., Proc. Natl. Acad. Sci. USA 81:2237-2241 (1984); Zurawski, U. R., et al., Fed. Proc. 39:1204 (1980)).

The typical staining patterns of colon adenocarcinomas and LS-180 obtained from a xenografted tumor in a nude mouse were compared to a normal nucosal counterpart. All tumors demonstrated a diffuse cellular staining pattern. Indeed 17 of 17 cases (100%) of colonic adenocarcinomas obtained from surgical specimens and examined as fresh frozen sections expressed SF-25 antigen in the primary tumor. Most if not all, tumor cells were stained; adjacent normal mucosa did not stain which further confirms the membrane binding studies presented in FIG. 2. A number of normal tissues were also found to be negative by immunoperoxidase staining including esophagus, stomach, small and large intestine, thyroid, lung, liver, pancreas, adrenal gland, skeletal muscle and myocardium. The kidney was examined in detail. No staining was observed in the glomerulus, proximal tubule or connective tissue. Staining was present in a subpopulation of distal tubular cells and the pattern was diffuse and cytoplasmic. Sections of LS-180 tumors grown in nude mice and human adenocarcinoma of the colon fixed with paraformaldehyde and subsequently paraffin embedded did not stain indicating that the antigen recognized by SF-25 is labile.

EXAMPLE 5

In Vivo Detection of Colon Adenocarcinomas

For nuclear imaging studies 150 to 250 Ci of $^{125}I$-labeled intact antibodies were injected i.v. via the tail vein into nude mice when LS180 tumors reached the size about 10 mM in diameter. The same amount of $^{125}I$-labeled intact $B_2TT$ were injected into tumor bearing mice as a control. Nude mice were anesthetized with 0.1 ml 4% chloral hydrate per 10 g body weight via intraperitoneal injection. Each nude mouse and then imaged 4 cm from the back with a gamma camera equipped with a 3 mm pinhole collinator and interfaced to a computer.

Nuclear imaging of LS-180 tumors was performed. Images were obtained at 6, 24, 48, 72 and 120 hours. In these experiments 150 to 250 Ci of $^{125}I$-labeled intact SF-25 or equivalent concentrations of intact $^{125}I$-labeled non-specific $B_2TT$ were injected i.v. into nude mice when tumors reached a size of 1.0 cm in diameter. Radiolabeled SF-25 clearly visualized the xenografted human colon cancer in nude mice and blood pool images by lung, heart or liver were not prominent compared with high intensity imaging of tumors. In contrast, no specific localization was observed with $^{125}I$-$B_2TT$ and the tumor was not visualized.

EXAMPLE 6

Identification of SF-25 Antigen

The presence of SF-25 antigen on the surface of FOCUS cells was examined by immunoprecipitation of $^{125}I$-labeled cell surface proteins. Cell surface labeling was performed by the lactoperoxidase method (Soule, H. R., et al., Int. J. Canc. 29:337-344 (1982)). In brief, a confluent 75 $cm^2$ monolayer culture was recovered by incubating with a EDTA/versene buffer for 5-10 minutes. The cell pellet was washed twice with 20 mM PBS pH 7.2 and brought to 0.5 ml. To the cell suspension, 1 mCi of $Na^{125}I$ and 40 g lactoperoxidase were added. The reaction was started by adding 15 Ml of 0.04% hydrogen peroxide and continued for 20 minutes by adding hydrogen peroxide every 5 minutes. To stop the reaction, 0.02M potassium iodide was added and the cells were washed twice in PBS. Thereafter, the cell pellet was lysed by incubating for 45 minutes in 0.1M PBS pH 7.2 containing 10 mM EDTA, 10 mM EGTA, 1% Triton ×100, 10 mM NaF, and 0.1% deoxycholate.

For the immunoprecipitation, covalently linked Mabs to protein A-Sepharose beads were used as described (Schneider, C., et al., J. Biol. Chem. 257:10766-10769 (1982)). Ascites fluid was dialyzed overnight against 0.1M sodium borate buffer pH 8.2 and one volume of the dialyzed fluid was incubated with one volume of beads in the same buffer for 16 hours at 4° C. The beads were then washed with 0.2M triethanolamine buffer pH 8.2 and incubated in the same buffer containing 30 mM dimethylpimilimdate for 45 minutes at 4° C. The beads were finally washed in 30 mM ethanolaine 0.2M triethanolamine pH 8.2 buffer and stored in 20 mM PBS pH 7.2 at 4° C. After incubating cell lysates with formalin-fixed Staphylococcus A cells for one hour at 4° C. and with the non-specific Mab linked-beads for two hours at 4° C., the immunoprecipitation was carried out overnight at 4° C. using specific Mab linked-beads. The beads were then washed and resuspended in 100 g of SDS polyacrylamide gel electrophoresis (PAGE) buffer (0.025M Tris-HCL buffer pH 8.8 containing 0.1% SDS and 20% glycerol), heated at 95° C. for 5 minutes and were electrophoresed on a 10% polyacrylamide slab gel (Laemmli, U. K., et al., Nature 277:680-685 (1970)). Gels were fixed, stained, destained, dried, and autoradiographed for 12 hours to 2 days by using Kodak X-ray film XOMAT-AR (Eastman Kodak Co., Rochester, N.Y.).

Using the above-described technique, the membrane proteins of living cells were radioiodinated, extracted by detergent and immunoprecipitated with SF-25 linked Sepharose beads. A protein of approximately 125 kd was isolated from FOCUS cell membranes.

EXAMPLE 7

In Vivo Biodistribution of SF-25:

Ten $\mu$Ci of $^{125}I$-SF-25 was injected I.V. via the tail vein into nude mice bearing human (LS-180) colon tumors. For dual tracer studies (Pressman, D., et al., Canc. Res. 17:845-850 (1957)), the mice were given simultaneous injections of 10 $\mu$Ci of $^{125}I$-SF-25 and 1 $\mu$Ci of $^{131}I$-$B^2TT$, a non-specific antibody. The mice were sacrificed and dissected at 24, 48, and 72 hours after injection. Tumors, blood, thyroid, heart, lung, kidney, stomach, intestine, liver and spleen were weighed on an analytical balance and assayed for radioactivity using a multichannel gamma counter (a window from 15 to 50 Kev for $^{125}I$ and a window from 50 to 330 Kev for $^{131}II$).

Figure 5:
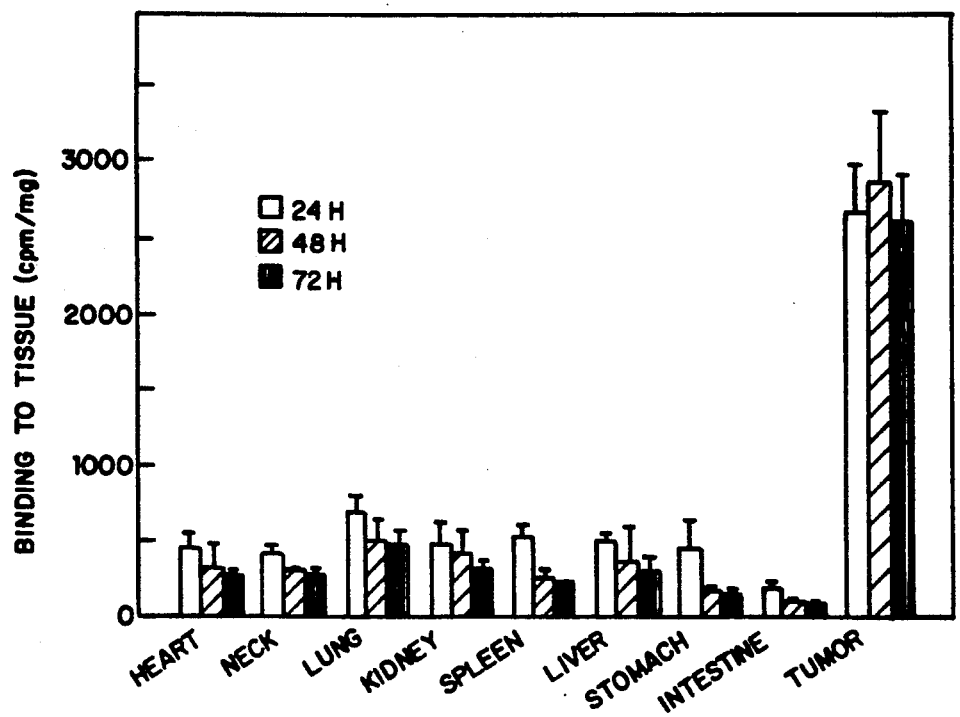
FIG. 5 shows the biodistribution of $^{125}$I-SF-25 in nude mice bearing LS-180-generated adenocarcinomas of the colon. Each timepoint represents the average values of three mice.
Figure 6:
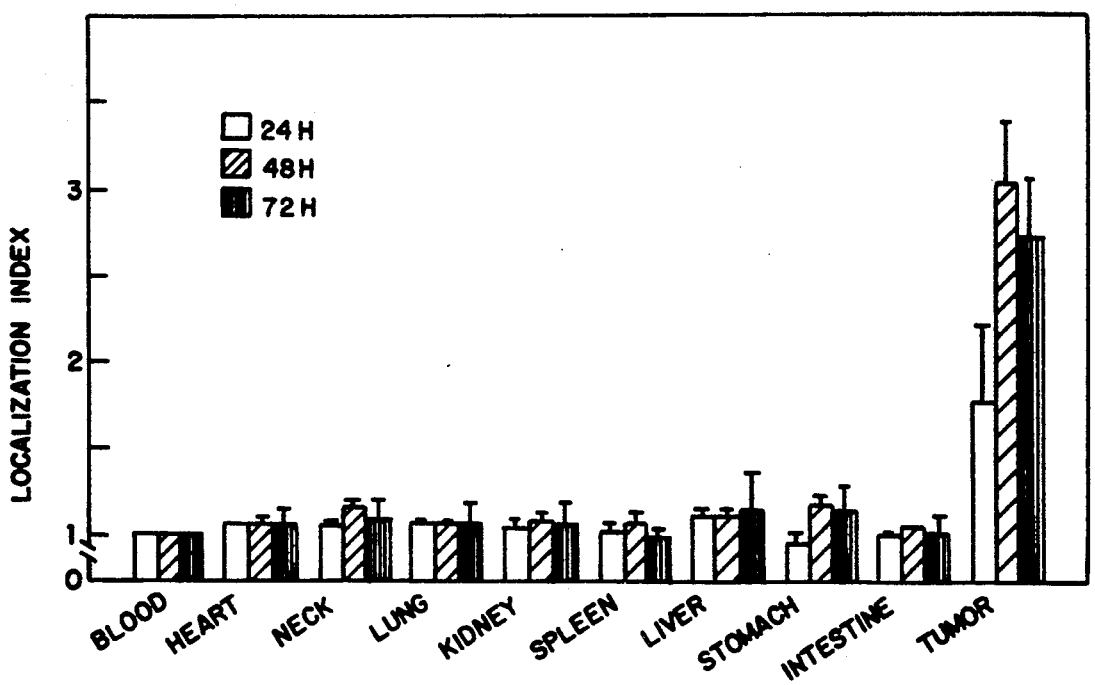
FIG. 6 shows the specific localization of $^{125}$I-SF-25 to tumor compared to an $^{131}$I-labeled control monoclonal antibody. The localization index is a ratio of these two values.

The specific activity in tumor was compared to other normal mouse tissues (FIG. 5); colon tumors showed a high uptake. It is noteworthy that tumor activity increased at 48 hours whereas in normal tissues antibody binding gradually decreased as a function of time after the injection of radiolabeled antibody. As depicted in Table 2, tumor/tissue ratios were maximal at 48 hours and were found to be 32.4 ±5.1 intestine, 20.6±6.2 stomach, 9.5±3.4 liver, 12.6±2.2 spleen, 7.9±2.0 kidney, 6.3±1.8 lung, 9.7±1.0 thyroid and 9.8±1.8 heart. H Further evidence of specific localization of Mab SF-25 was established by comparing $^{125}$I-labeled SF-25 and $^{131}$I-labeled non-specific Mab (B$_2$TT) injected simultaneously into tumor bearing mice (FIG. 6). The localization indices derived from the ratio of specific to nonspecific activity in tumor divided by the same ratio in the blood were 1.81±0.46 (24 hours), 3.07±0.34 (48 hours), and 2.75±0.33 (72 hours), demonstrating specific localization in colon cancer by 48 hours ($P<0.001$). The localization indices of all normal tissues tested varied between 0.97 and 1.19, reflecting a selective and specific binding of $^{125}$I-SF-25 to human colon tumors compared to a $^{131}$I-B$_2$TT non-specific Mab.

TABLE 2

Uptake of SF25 in Adenocarcinoma of Colon Compared to Normal Tissues
Tumor/Tissue $^{125}$I-SF25

| Organ | 24 h | 48 h | 72 h |
| --- | --- | --- | --- |
| Tumor | 1.00 | 1.00 | 1.00 |
| Heart | 6.17 ± 1.67 | 9.84 ± 1.75 | 10.78 ± 3.04 |
| Neck | 6.69 ± 1.30 | 9.73 ± 0.97 | 9.92 ± 2.49 |
| Lung | 3.94 ± 0.78 | 6.31 ± 1.77 | 5.77 ± 1.50 |
| Kidney | 5.97 ± 1.34 | 7.88 ± 2.05 | 8.67 ± 2.00 |
| Spleen | 5.29 ± 1.37 | 12.60 ± 2.21 | 12.67 ± 1.98 |
| Liver | 5.48 ± 1.10 | 9.48 ± 3.40 | 9.82 ± 3.91 |
| Stomach | 7.47 ± 4.51 | 20.58 ± 6.15 | 18.50 ± 1.32 |
| Intestine | 14.85 ± 2.00 | 32.43 ± 5.07 | 31.77 ± 4.17 |

EXAMPLE 8

Western Blot Analysis

Antigenic extracts were prepared from cultured cell lines and from human tissues as follows. Normal human tissue were obtained from a cadaver within 6 hours after death. Human tumor tissues were obtained from surgical specimens, snap-frozen and kept at −80° C. until use. Confluent cells were harvested from culture flasks using EDTA/versene buffer without proteolytic enzymes, washed twice in PBS and suspended in ice-cold 0.1M Tris-HCl buffer pH 8 containing 0.5% NP40, 0.1M NaCl, and 0.1% aprotinin. After 10 minutes incubation on ice, lysates were centrifuged for 15 minutes at 1500 g at 4° C. Supernatant was harvested, adjusted to a protein concentration of 1 mg/ml, and stored frozen at −80° C. until use. Tissue samples were homogenized using a Potter apparatus in 10 volumes of ice-cold 0.1M Tris-HCl buffer pH 8 containing 0.1M NaCl and 0.1% aprotinin. NP 40 (0.5%) was then added and samples were incubated on ice for 15 minutes and centrifuged at 10,000 g for 10 minutes at 4° C. Supernatant was harvested, adjusted to a protein concentration of 1 mg/ml, and stored at −80° C. until use. For SDS-polyacrylamide gel electrophoresis (SDS-PAGE), the protein preparations were incubated for 5 minutes at 90° C. in a SDS-PAGE buffer and 50 µg of protein was loaded at the top of a 10% SDS polyacrylamide gel and separated according to Laemmli (12). The proteins were electrophoretically transferred onto nitrocellulose paper. The paper was then incubated with 1:100 dilution of SF-25 ascites fluid and subsequently with $^{125}$I -labeled sheep anti-mouse immunoglobulin F(ab)$_2$ and was exposed for autoradiography.

These experiments failed to identify SF-25 antigen, a finding which suggests that SF-25 is either a labile epitope, inefficiently extracted from the membrane, or expressed at an extremely low level.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

We claim:

1. A molecule which specifically binds to the SF-25 antigen of a colon adenocarcinoma cell, said molecule being selected from the group consisting of:
   (a) an antibody substantially free of natural contaminants;
   (b) a monoclonal antibody;
   (c) a fragment of (a) or (b).

2. The molecule of claim 1, wherein said molecule is said antibody substantially free of natural contaminants.

3. The molecule of claim 1, wherein said molecule is said monoclonal antibody.

4. The molecule of claim 1, wherein said molecule is said fragment of an antibody.

5. The molecule of claim 1, wherein said molecule is a fragment of said monoclonal antibody.

6. The molecule of claim 1, wherein said fragment is an F(ab)$_2$ fragment.

7. The molecule of claim 1, wherein said fragment is an F(ab) fragment.

8. The molecule of claim 1, wherein said molecule is labeled with a detectable moiety.

9. A hybridoma cell line which secretes a monoclonal antibody, said antibody specifically binding to the SF-25 antigen of a colon adenocarcinoma cell.

10. The hybridoma cell line of claim 9, which is ATCC strain HB 9599.

11. The monoclonal antibody obtainable from the hybridoma cell line of claim 9.

12. The monoclonal antibody obtainable from the hybridoma cell line of claim 10.

* * * * *

UNITED STATES PATENT AND TRADEMARK OFFICE
CERTIFICATE OF CORRECTION

PATENT NO. : 5,212,085

ISSUED : May 18, 1993

INVENTORS : Wands et al.

It is certified that errors appear in the above-identified patent and that said Letters Patent is hereby corrected as shown below.

*In the Title*

On the title page, item [54], on line 2, please remove "WITH" and replace therewith --WHICH--; and item [75], line 6, please remove "Walrun" and replace therewith --Waban--.

In column 1, line 3, please remove "WITH" and replace therewith --WHICH--.

In column 3, line 8, please remove "bovarian" and replace therewith --ovarian--.

In column 7, line 33, please remove "17.IA" and replace therewith --17.1A--.

In column 8, line 33, please remove "coloni" and replace therewith --colonic--.

In column 15, line 42, please remove "qal" and replace therewith --gal--.

In column 17, line 33, please remove "$^{131}$-labeled" and replace therewith --$^{131}$I-labeled--; and line 45, please remove "$^{162}$" and replace therewith --$^{162}$Dy--.

In column 23, line 67, please remove "$^{125}$" and replace therewith --$^{125}$I--.

UNITED STATES PATENT AND TRADEMARK OFFICE
CERTIFICATE OF CORRECTION

PATENT NO. : 5,212,085

ISSUED : May 18, 1993

INVENTORS : Wands et al.

It is certified that errors appear in the above-identified patent and that said Letters Patent is hereby corrected as shown below.

In column 25, line 33, please remove "*vivo*" and replace therewith --*vero*--.

In column 27, line 17, please remove "nucosal" and replace therewith --mucosal--.

In column 28, line 26, please remove "dimethylpimilimdate" and replace therewith --dimethylpimilimidate--; and line 27, please remove "ethanolaine" and replace therewith --ethanolamine--.

In column 29, line 9, please remove "H".

Signed and Sealed this

Fifth Day of April, 1994

Attest:

BRUCE LEHMAN

Attesting Officer     Commissioner of Patents and Trademarks